(12) United States Patent
Qiu (10) Patent No.: US 10,779,575 B2
(45) Date of Patent: Sep. 22, 2020

(54) ATOMIZER AND AEROSOL GENERATING DEVICE THEREOF

(71) Applicant: JOYETECH EUROPE HOLDING GMBH, Zug (CH)

(72) Inventor: Weihua Qiu, Jiangsu (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 315 days.

(21) Appl. No.: 15/897,916

(22) Filed: Feb. 15, 2018

(65) Prior Publication Data
US 2018/0168236 A1    Jun. 21, 2018

Related U.S. Application Data

(63) Continuation of application No. PCT/IB2016/055038, filed on Aug. 24, 2016.

(30) Foreign Application Priority Data

Aug. 26, 2015 (CN) .................... 2015 2 0646073 U (51) Int. Cl.
*A24F 47/00* (2020.01)
*A61M 11/04* (2006.01)
(Continued)

(52) U.S. Cl.
CPC ......... *A24F 47/008* (2013.01); *A61M 11/042* (2014.02); *A61M 15/002* (2014.02); *A61M 15/06* (2013.01); *A61M 2205/3653* (2013.01)

(58) Field of Classification Search
CPC ... A24F 47/008; A61M 15/06; A61M 11/042; A61M 2205/3653; A61M 2205/8206;
(Continued)

(56) References Cited

U.S. PATENT DOCUMENTS

2014/0261500 A1   9/2014  Park
2015/0136157 A1   5/2015  Liu

FOREIGN PATENT DOCUMENTS

CN    204157650 U    2/2015
CN    204217908 U    3/2015
WO    2015062136 A1  5/2015

OTHER PUBLICATIONS

English translation of CN204157650 (Year: 2014).*
English translation of WO2015062136 (Year: 2015).*

* cited by examiner

*Primary Examiner* — Serkan Akar
*Assistant Examiner* — Chris Q Liu
(74) *Attorney, Agent, or Firm* — Novick, Kim & Lee, PLLC; Allen Xue (57) ABSTRACT

An atomizer includes an upper cover assembly, an atomizing device and a regulating assembly. The atomizing device is arranged between the upper cover assembly and the regulating assembly. The regulating assembly includes a regulating base and a regulating ring rotatably sleeved about the regulating base. The regulating base is provided with at least one first circulating portion in fluid communication with the atomizing device. The regulating ring is provided with a second circulating portion arranged corresponding to the first circulating portion. An area of communication between the first circulating portion and the second circulating portion is changed by rotating the regulating ring. The atomizer has a good leak-proof function.

10 Claims, 9 Drawing Sheets

(51) Int. Cl.
*A61M 15/06* (2006.01)
*A61M 15/00* (2006.01)

(58) Field of Classification Search
CPC .............. A61M 15/002; A61M 11/007; A61M 15/025; A61M 2016/0024; A61M 2016/0039; A61M 2205/584
USPC .......................... 392/394, 404, 386, 397, 534
See application file for complete search history.

ATOMIZER AND AEROSOL GENERATING DEVICE THEREOF

CROSS-REFERENCE TO RELATED APPLICATIONS

This application is a continuation application of International Patent Application NO. PCT/IB2016/055038, filed on Aug. 24, 2016, which claims priority to Chinese Patent Application NO. CN201520646073.8, filed on Aug. 26, 2015.

FIELD

The present disclosure relates to an aerosol generating device and, in particular, to an atomizer capable of avoiding liquid leakage and an aerosol generating device thereof.

BACKGROUND

An electronic cigarette is known as a virtual cigarette or an electronic atomizer, which acts as one of electrical heating aerosol generating devices. Currently, the existing electronic cigarettes in the market generally have a problem of liquid leakage, reasons for which include various aspects, where a main reason lies in that it is easy for liquid to leak out from a liquid storage chamber through an atomizing assembly. After the liquid is leaked out, on one hand, the user may taste the liquid during smoking, which affects smoking experience of the user; on the other hand, the liquid may also leak to a battery and/or a control panel, which affects normal operations of the electronic cigarette.

Most of the existing electronic cigarettes accomplish leak-proof by adding a leak-proof mechanism. However, the structure is relatively complex and has a low reliability.

SUMMARY

Accordingly, it is necessary to provide an atomizer capable of avoiding liquid leakage and an aerosol generating device thereof with regard to the above problem.

An atomizer includes an upper cover assembly, an atomizing device and a regulating assembly. The atomizing device is arranged between the upper cover assembly and the regulating assembly. The regulating assembly includes a regulating base and a regulating ring rotatably sleeved about the regulating base. The regulating base is provided with at least one first circulating portion in fluid communication with the atomizing device. The regulating ring is provided with a second circulating portion arranged corresponding to the first circulating portion. The area of communication between the first circulating portion and the second circulating portion can be changed by rotating the regulating ring.

In one embodiment, an upper edge of the regulating ring bends inwardly to form an annular holding portion. The holding portion abuts an upper end of the regulating base. The holding portion is provided with the second circulating portion. The second circulating portion is at least partially aligned with the first circulating portion by rotating the regulating ring, which enables the atomizing device to be in fluid communication with the regulating assembly.

In one embodiment, the atomizer further includes a collecting device arranged in the regulating assembly. The collecting device includes a retaining portion, a tubular body and a collecting slot. One end of the tubular body extends towards the inside of the tubular body to form the retaining portion, and the retaining portion is fixedly connected to the tubular body to form the collecting slot. The collecting device has a simple structure and can protect the atomizer from liquid leakage.

In one embodiment, an angle formed between the tubular body and the retaining portion is between 0-90 degrees.

In one embodiment, the retaining portion is bowl-shaped or funnel-shaped.

In one embodiment, the atomizing device further includes an accommodating tube, an atomizing tube, an accommodating cavity, an atomizing base, an air-intake pipe, and an atomizer head. The atomizing tube is arranged in the accommodating tube. The atomizing base is disposed at the end of the accommodating tube away from the upper cover assembly. The accommodating cavity is formed among the accommodating tube, the atomizing tube and the atomizing base. The air-intake pipe is located in the accommodating cavity. One end of the atomizing tube is tightly fitted with the atomizer head, and the other end of the atomizing tube is disposed on the upper cover assembly.

In one embodiment, the upper cover assembly includes an upper cover, an upper cover connecting base and an air inlet defined on the upper cover. The upper cover connecting base is fixedly connected between the upper cover and the atomizing device.

In one embodiment, the upper cover connecting base is provided with a fixing hole. The air-intake pipe extends through the fixing hole and is affixed in the fixing hole, and the other end of the air-intake pipe is disposed on the atomizing base.

In one embodiment, the atomizing base includes a shoulder, a first connecting portion and a second connecting portion, where the first connecting portion and the second connecting portion are connected to opposite ends of the shoulder, respectively. The first connecting portion is connected to a connecting ring. The second connecting portion is connected to the regulating assembly. The atomizer head is threadedly arranged onto the atomizing base by means of the connecting ring.

An aerosol generating device includes an atomizer according to any one hereinabove.

According to the atomizer and the aerosol generating device applying the same in the present disclosure, there are following advantages:

The atomizer accomplishes air intake from the top and air regulation at the bottom simultaneously. That is, after entering from the top or the side of the atomizer, the airflow flows to the bottom of the atomizing device through the air-intake pipe, and then the airflow is regulated by means of the regulating ring at the bottom. Such a design avoids forming a low pressure at the bottom the atomizing device due to the suction, thereby effectively preventing liquid leakage due to the low pressure resulting from air intake at the bottom of the atomizing device.

REFERENCE NUMERALS

| | |
|---|---|
| atomizer 100 | cigarette holder 10 |
| upper cover assembly 20 | atomizing device 30 |
| regulating assembly 70 | first sealing ring 11 |
| upper cover 21 | upper cover connecting base 23 |
| air inlet 25 | fixing hole 27 |
| accommodating cavity 35 | atomizing base 37 |
| second sealing ring 38 | air-intake pipe 39 |
| connecting ring 41 | atomizing cavity 43 |
| atomizer head 45 | outer tube 47 |
| first connecting portion 373 | second connecting portion 375 |
| connecting tube 377 | through hole 379 |
| air vent 453 | regulating base 71 |
| regulating ring 73 | first circulating portion 711 |
| stopping boss 712 | holding portion 731 |
| second circulating portion 733 | collecting device 80 |
| matching hole 81 | retaining portion 83 |
| tubular body 85 | collecting slot 87 |
| conductive assembly 60 | positive electrode contact 61 |
| insulator 63 | atomizing tube 33 |
| accommodating tube 31 | shoulder 371 |
| liquid inlet 451 | connecting hole 51 |

DETAILED DESCRIPTION

In order to make the above described objectives, characteristics and advantages of the present disclosure clearer and easy to understand, specific implementations of the present disclosure will be described hereunder in detail with reference to the accompanying drawings. In the following description, many details are described for facilitating comprehensive understanding of the present disclosure. However, the present disclosure can be implemented in many ways other than those described herein. Persons skilled in the art can make similar improvements without departing from the connotation of the present disclosure. Therefore, the present disclosure is not limited to the following disclosed embodiments.

It should be noted that, when an element is referred to as "being fixed to" another element, it can be directly located on another element or there may be a centered element therebetween. When an element is considered as "being connected to" another element, it can be directly connected to another element or there may be a centered element therebetween at the same time.

Unless defined otherwise, all the technical and scientific terms used herein have same meanings as those commonly understood by technical persons belong to the technical field of the present disclosure. Herein, the terms used in the description of the present disclosure are only for the purpose of describing specific embodiments, rather than limiting the present disclosure. The term "and/or" used herein includes any and all combinations of one or more associated listed items.

Referring to FIGS. 1, 2, 4 and 5, the present disclosure provides an atomizer 100, which comprises an upper cover assembly 20, an atomizing device 30, a conductive assembly 60 and a regulating assembly 70. The atomizing device 30 is located between the upper cover assembly 20 and the regulating assembly 70. The conductive assembly 60 is disposed about the regulating assembly 70, and is electrically connected to the atomizing device 30.

Figure 6:
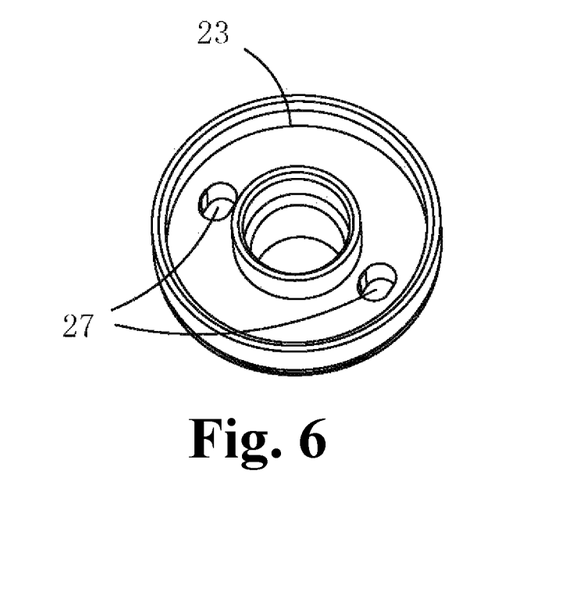
FIG. 6 is a perspective view of the upper cover connecting base as shown in FIG. 2.

Referring to FIG. 6 in combination, the upper cover assembly 20 includes an upper cover 21, an upper cover connecting base 23 and an air inlet 25 defined on the upper cover 21. The upper cover connecting base 23 is fixedly connected between the upper cover 21 and the atomizing device 30 when assembled. The upper cover connecting base 23 is further provided with two fixing holes 27.

Figure 2:
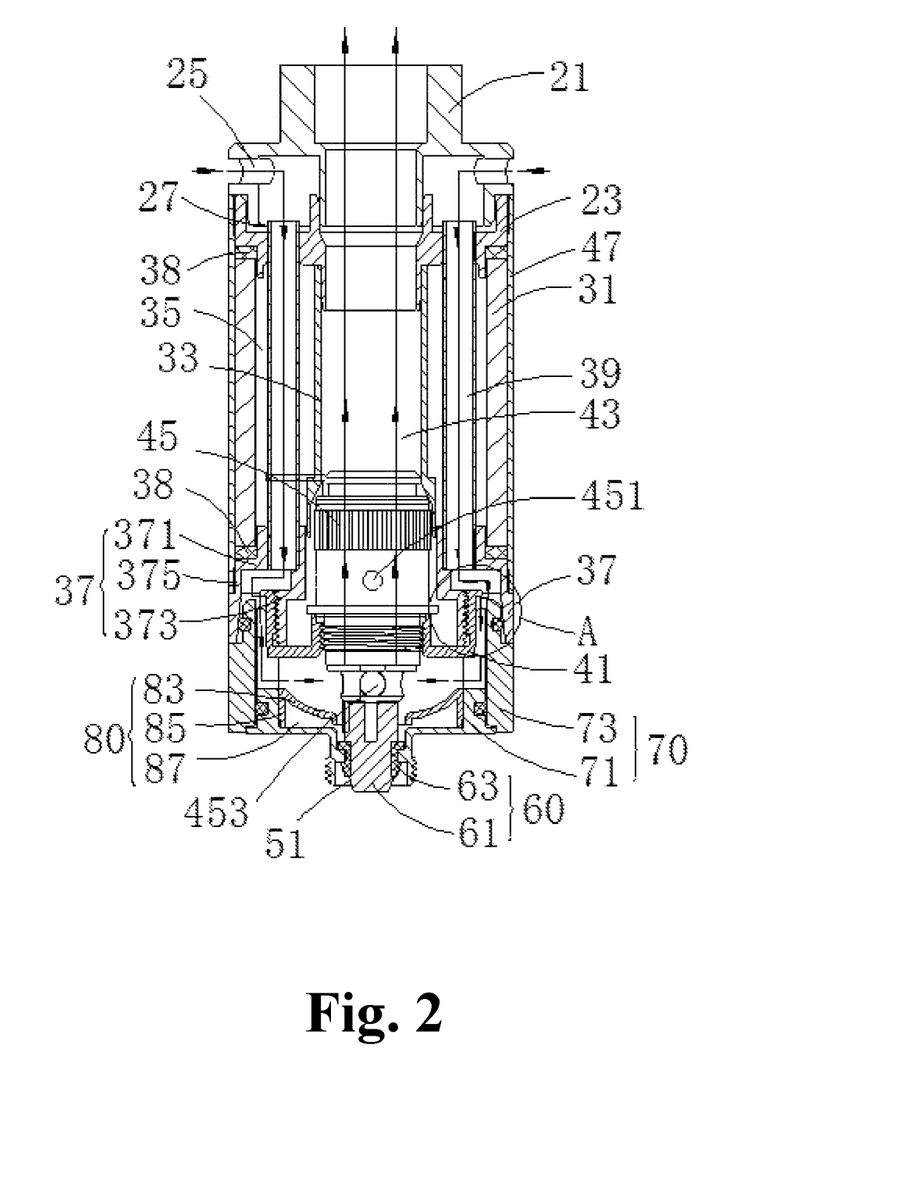
FIG. 2 is a sectional view of the atomizer (without a cigarette holder) as shown in FIG. 1.
Figure 4:
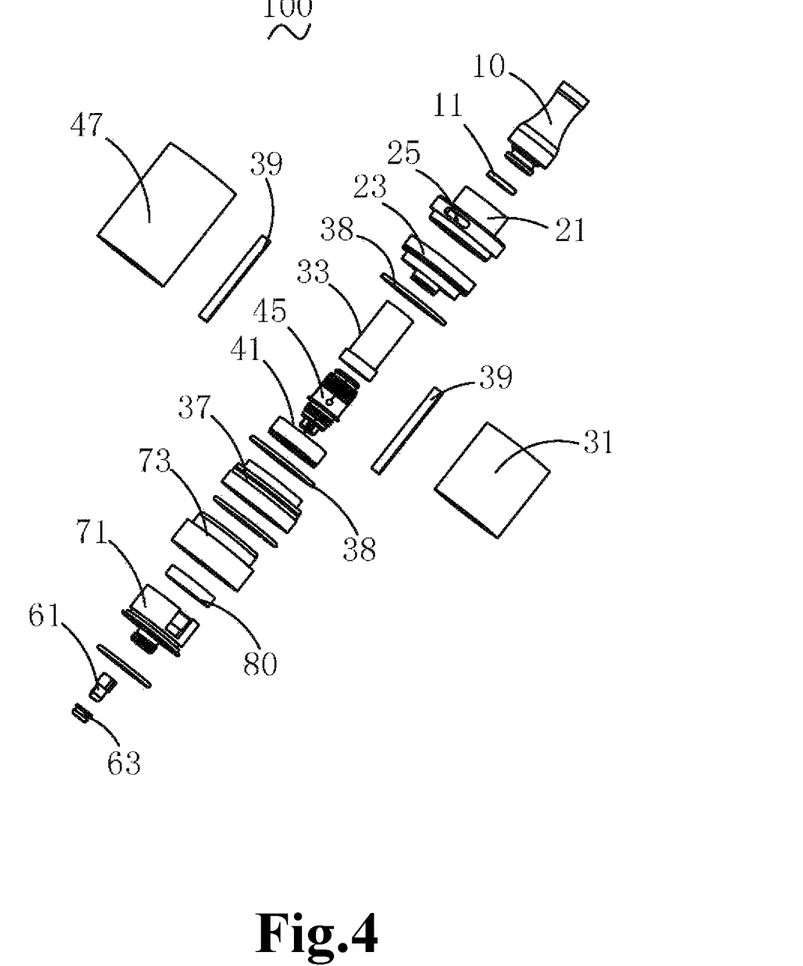
FIG. 4 is an exploded perspective view of the atomizer as shown in FIG. 1.
Figure 5:
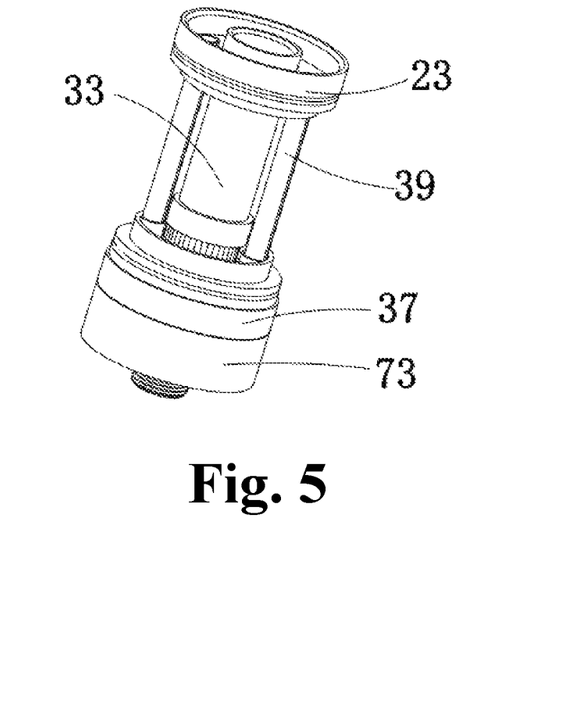
FIG. 5 is a local perspective view of the atomizer as shown in FIG. 1.

The atomizing device 30 includes an accommodating tube 31, an atomizing tube 33, an accommodating cavity 35, an atomizing base 37, an air-intake pipe 39, a connecting ring 41, an atomizing cavity 43, an atomizer head 45, and an outer tube 47. The atomizing tube 33 is arranged in the accommodating tube 31. One end of the atomizing tube 33 is tightly fitted with the atomizer head 45, and the other end of the atomizing tube 33 is disposed on the upper cover assembly 20. The atomizer head 45 is threadedly connected to the atomizing base 37 through the connecting ring 41. That is, an inner side of the connecting ring 41 is threadedly connected with the atomizer head 45, and an outer side of the connecting ring 41 is threadedly connected with the atomizing base 37. The accommodating cavity 35 is formed among the accommodating tube 31, the atomizing tube 33, the atomizer head 45 and the atomizing base 37. Each air-intake pipe 39 is arranged in the accommodating cavity 35, one end thereof is affixed to the fixing hole 27, and the other opposite end thereof is disposed on the atomizing base 37.

The outer tube 47 is sleeved outside the accommodating tube 31. An end of the outer tube 47 is disposed on the atomizing base 37, and the other end of the outer tube 47 is disposed on the upper cover assembly 20. In this embodiment, the accommodating tube 31 is made of a transparent or semi-transparent material. The outer tube 47 is provided with a window (not shown in the figures) for making it convenient for a user to observe the liquid level within the accommodating cavity 35.

One end of the accommodating tube 31 abuts the upper cover assembly 20, and the other opposite end thereof abuts the atomizing base 37. Such that the accommodating tube 31 is disposed between the atomizing base 37 and the upper cover assembly 20. In this embodiment, two sealing rings 38 are provided between the accommodating tube 31 and the upper cover assembly 20 and between the accommodating tube 31 and the atomizing base 37, respectively. The sealing rings 38 are used to improve sealing properties of the accommodating cavity 35 to avoid liquid leakage.

The atomizing base 37 includes a shoulder 371, a first connecting portion 373 and a second connecting portion 375, where the first connecting portion 373 and the second connecting portion 375 are connected to opposite ends of the shoulder 371, respectively. The first connecting portion 373 is connected to the connecting ring 41, and the second connecting portion 375 is connected to the regulating assembly 70. In this embodiment, the relation between the first connecting portion 373 and the connecting ring 41 is a threaded connection, and the second connecting portion 375 and the regulating assembly 70 is in an interference fit.

Further, the end of the accommodating tube 31 close to the atomizing base 37 abuts the shoulder 371. The accommodating cavity 35 is defined by the accommodating tube 31, the second connecting portion 375, the atomizer head 45 and the atomizing tube 33. The atomizer head 45 is provided with a liquid inlet 451, and liquid within the accommodating cavity 35 may enter the atomizer head 45 via the liquid inlet 451.

Figure 7:
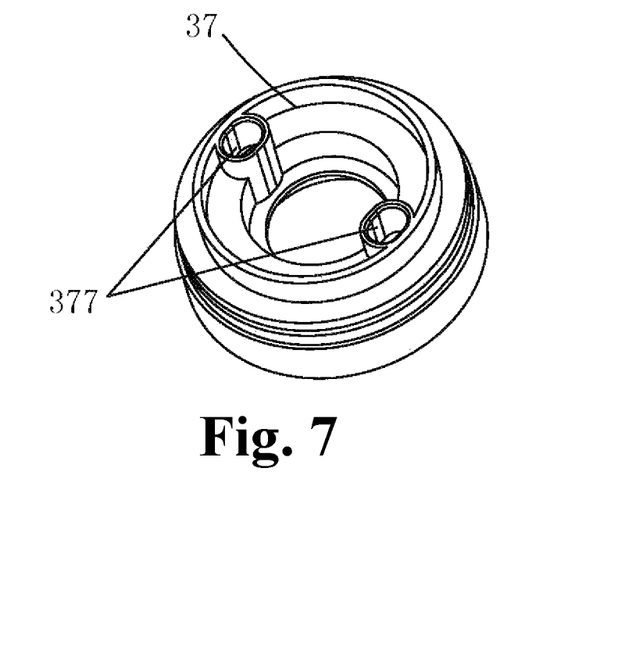
FIG. 7 is a perspective view of the atomizing base as shown in FIG. 2.
Figure 8:
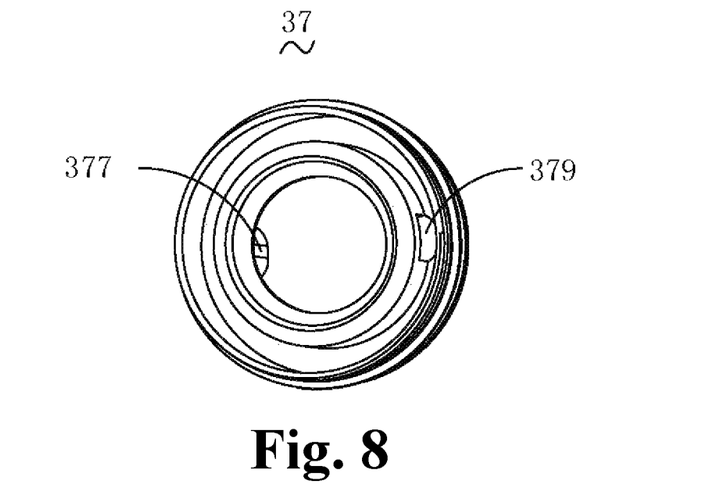
FIG. 8 is a perspective view of the atomizing base as shown in FIG. 2 in another direction.
Figure 9:
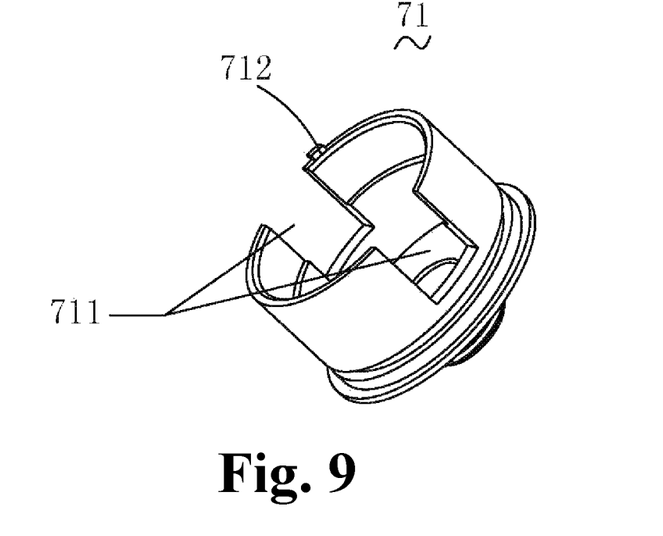
FIG. 9 is a perspective view of the regulating base as shown in FIG. 2.
Figure 10:
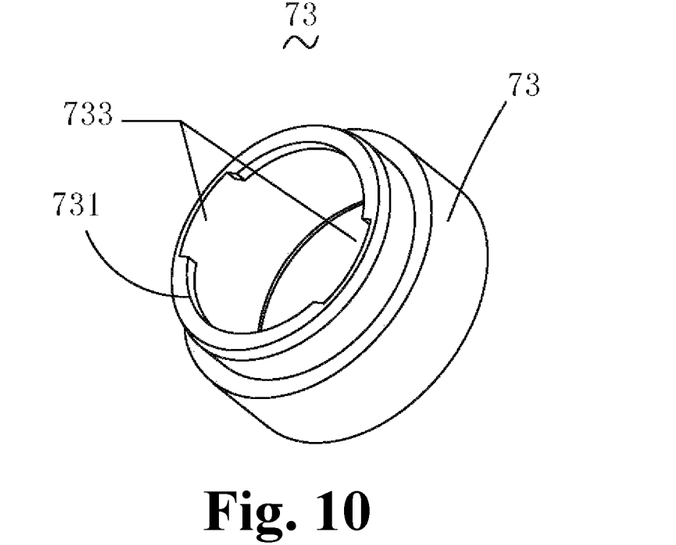
FIG. 10 is a perspective view of the regulating ring as shown in FIG. 2.

Further referring to FIGS. 7, 8, the atomizing base 37 is provided with two connecting tubes 377. Each connecting tube 377 is sleeved on and in fluid communication with one of the air-intake pipes 39. The shoulder 371 is provided with two through holes 379, and each of the through holes 379 is in fluid communication with the corresponding connecting tube 377. The atomizer head 45 is provided with an air vent 453 in fluid communication with the through holes 379. Under suction of the user, the air entering the air-intake pipes 39 may enter the atomizer head 45 via the connecting tubes 377, the through holes 379 and the air vent 453, then the air will take away smoke formed by atomization of the atomizer head 45.

The conductive assembly 60 is used to enable the atomizer 100 to be electrically connected to a power source (not shown in the figures). The regulating assembly 70 is provided with a connecting hole 51, and the conductive assembly 60 passes through the connecting hole 51 to be in electrical contact with the atomizer head 45 and the power source, respectively. Specifically, the conductive assembly 60 includes a positive electrode contact 61 and an insulator 63. The insulator 63 is sleeved on the positive electrode contact 61. One end of the positive electrode contact 61 is in electrical connection with the atomizer head 45, and the other end of the positive electrode contact 61 passes through the connecting hole 51 to be in electrical contact with the power source for providing electric power to the atomizing device 30.

Referring to FIGS. 9-12, the regulating assembly 70 is used to regulate air inlet volume of the atomizer 100. The regulating assembly 70 includes a regulating base 71 and a regulating ring 73 rotatably sleeved about the regulating base 71. The regulating base 71 is provided with at least one first circulating portion 711 and a stopping boss 712 disposed near an opening of one of the first circulating portions 711. An upper edge of the regulating ring 73 bends inwardly to form an annular holding portion 731, and the holding portion 731 is provided with a second circulating portion 733 corresponding to the first circulating portion 711. The holding portion 731 abuts an upper end of the regulating base 71. In this embodiment, there are two first circulating portions 711, and the regulating ring 73 is also provided with two second circulating portions 733 corresponding to the first circulating portions 711. The stopping boss 712 protrudes into the second circulating portion 733 to enable the regulating ring 73 to rotate within a scope of the radian of the second circulating portion 733. In this embodiment, the radian of the second circulating portion 733 is larger than that of the first circulating portion 711.

Figure 3:
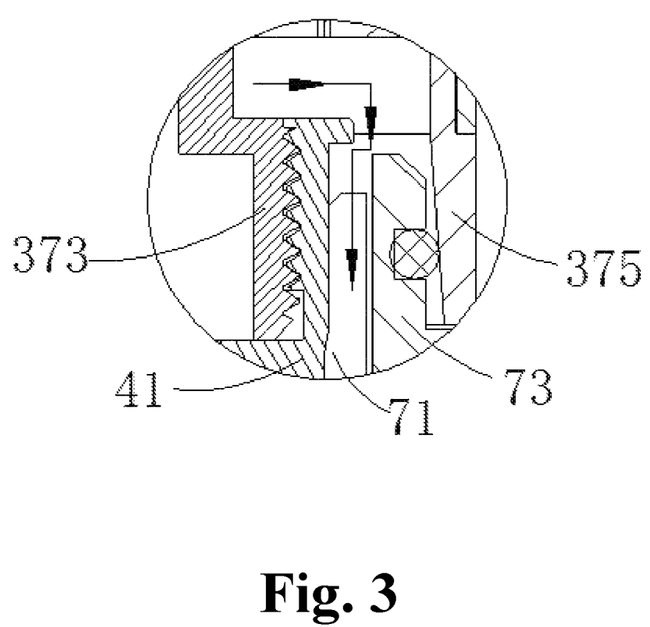
FIG. 3 is an enlarged view of the A-portion as shown in FIG. 2.
Figure 11:
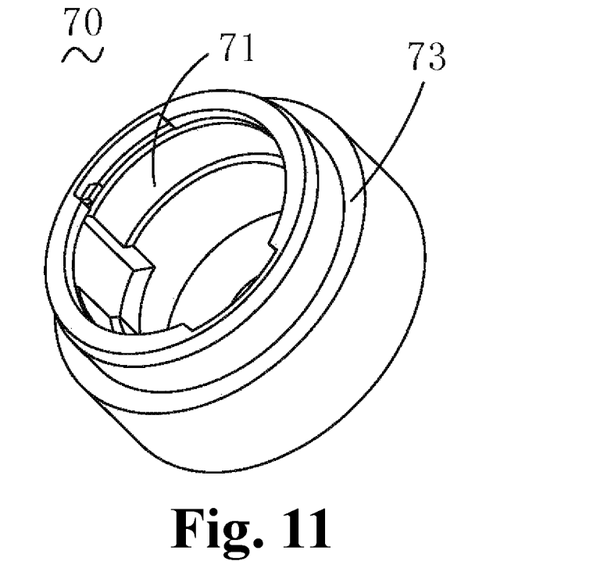
FIG. 11 shows the configuration of the regulating assembly when the second circulating portion is completely staggered with the first circulating portion.
Figure 12:
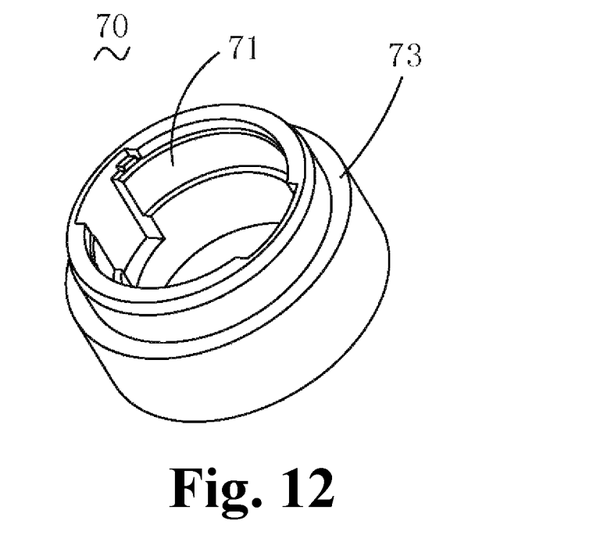
FIG. 12 shows the configuration of the regulating assembly when the second circulating portion is aligned with the first circulating portion.

The second circulating portion 733 may be staggered or aligned or in partial fluid communication with the first circulating portion 711 by rotating the regulating ring 73 so as to change size of the area in fluid communication between the atomizing device 30 and the regulating assembly 70, which regulates the air intake volume entering the atomizing device 30 from the first circulating portion 711 and the second circulating portion 733. Referring to FIG. 11 in combination, when the second circulating portion 733 is completely staggered with the first circulating portion 711, the holding portion 731 abuts both the opening of the first circulating portion 711 and an outer wall of the connecting ring 41, which seals the airflow passage and blocks the air entering the atomizer 100 via the air inlet 25 and the air-intake pipe 39 from entering the atomizer head 45 via the air vent 453. Referring to FIGS. 3 and 12 in combination, when the second circulating portion 733 is aligned with or in partial fluid communication with the first circulating portion 711, the air entering the atomizer 100 via the air inlet 25 and the air-intake pipe 39 may enter the atomizer head 45 via a space formed between the second circulating portion 733 and the first circulating portion 711 and via the air vent 453. Then the air carries with aerosols formed by atomization of the atomizer head 45 and is discharged via the atomizing cavity 43 and the cigarette holder 10, for inhalation by the user. The size of the communication space between the second circulating portion 733 and the first circulating portion 711 is regulated by rotating the regulating ring 73. In such a manner, the air inlet volume entering the atomizer head 45 can be regulated.

Figure 13:
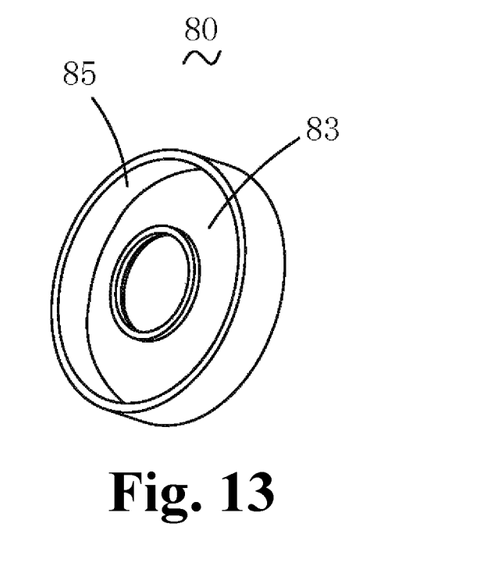
FIG. 13 is a perspective view of the collecting device as shown in FIG. 2.
Figure 14:
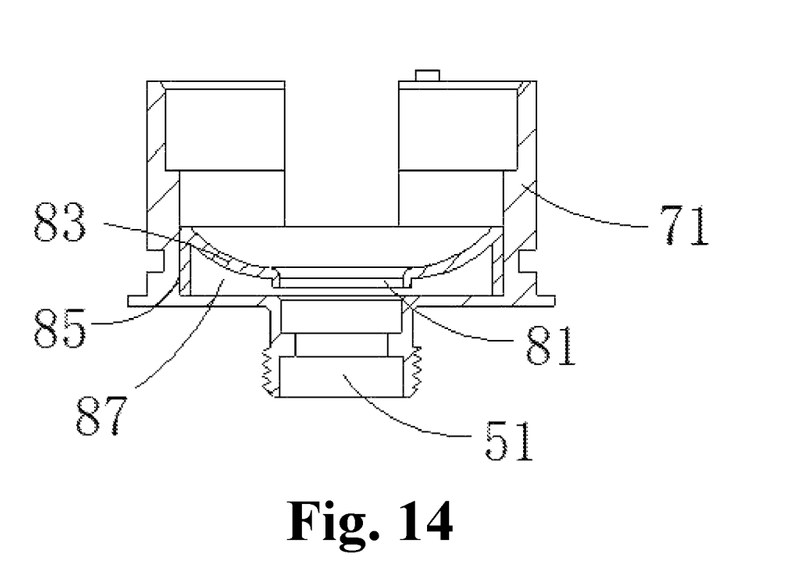
FIG. 14 is a sectional view of the collecting device and the regulating base as shown in FIG. 2.

Referring to FIGS. 13 and 14, the atomizer 100 further comprises a collecting device 80. The collecting device 80 is arranged in the regulating assembly 70 and is used to collect liquids such as smoke liquid leaked from the atomizer head 45 and the accommodating cavity 35 and condensed smoke. The collecting device 80 is provided with a matching hole 81, and the conductive assembly 60 may be in electrical contact with the power source by sequentially passing through the matching hole 81 and the connecting hole 51. A gap is formed between the matching hole 81 and the conductive assembly 60, which is used for liquids such as smoke liquid or condensed smoke to flow into a space formed between the collecting device 80 and the regulating assembly 70. Thus, the collecting device 80 has a simple structure and is capable of avoiding liquid leakage from occurring in the atomizer 100.

The collecting device 80 includes a retaining portion 83, a tubular body 85 and a collecting slot 87. The retaining portion 83 is a bowl-like or funnel-like body formed by an upper end of the tubular body 85 extending towards the inside of the tubular body 85. That is, the retaining portion 83 is substantially bowl-shaped or funnel-shaped. The matching hole 81 is defined in the center of the retaining portion 83. The retaining portion 83 is fixedly connected to the tubular body 85 to form the collecting slot 87, and inner walls of the retaining portion 83 and the tubular body 85 form slot walls of the collecting slot 87. When the atomizer 100 is placed upside down, liquids will flow into the bottom of the collecting slot 87. In such a manner, the liquids can be prevented from flowing back to the atomizer head 45 or the accommodating cavity 35.

In use, the user only needs to remove the regulating assembly 70 and the atomizer head 45 from the atomizing device 30, and then the atomizer 100 may be added or replaced with smoke liquid. In other words, a liquid injection method used by the atomizer 100 is liquid injection at the lower end or liquid injection at the bottom.

In the present disclosure, an angle formed between the tubular body 85 and the retaining portion 83 is between 0-90 degrees.

The atomizer 100 has the following advantages:

The atomizer 100 adopts air intake from the top and air regulation at the bottom simultaneously. That is, after entering from the top or the side of the atomizer 100, the airflow flows to the bottom of the atomizing device 30 through the air-intake pipe 39, and then the airflow is regulated by means of the regulating ring 73 at the bottom. Such a design prevents the atomizing device 30 from forming a low pressure at the bottom due to the suction, thereby effectively reducing the possibility of liquid leakage due to the low pressure resulting from air intake at the bottom of the atomizing device 30.

Figure 1:
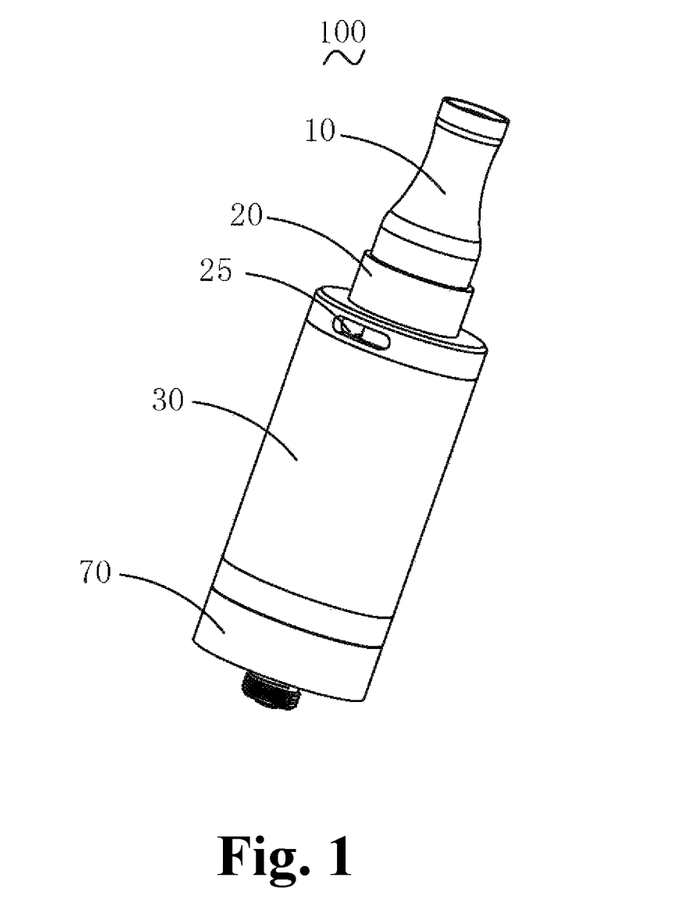
FIG. 1 is a schematic structural view of an atomizer according to the present disclosure.

The present disclosure further provides an aerosol generating device having the atomizer 100 according to any of the above. The aerosol generating device further includes a cigarette holder 10. The cigarette holder 10 is detachably mounted on the upper cover assembly 20. The cigarette holder 10 is provided with an accommodating slot (not labelled). The first sealing ring 11 is accommodated in the accommodating slot, which enables the cigarette holder 10 to be in close fit with the upper cover assembly 20 detachably.

The foregoing embodiments merely describe several implementations of the present disclosure with specific details, and should not be interpreted as a limitation to the present disclosure. It should be noted that, persons of ordinary skill in the art may make variants and modifications without departing from the conception of the present disclosure, and all of these variants and modifications fall into the protection scope of the present disclosure.

Accordingly, the protection scope of the present disclosure should be subject to the appended claims.

What is claimed is:

1. An atomizer comprising:
   an upper cover assembly;
   an atomizing device;
   a regulating assembly; and
   a collecting device arranged in the regulating assembly;
   wherein the atomizing device is arranged between the upper cover assembly and the regulating assembly, the regulating assembly comprises a regulating base and a regulating ring rotatably sleeved about the regulating base, the regulating base is provided with at least one first circulating portion in fluid communication with the atomizing device, the regulating ring is provided with a second circulating portion arranged corresponding to the first circulating portion, and an area of communication between the first circulating portion and the second circulating portion is changed by rotating the regulating ring,
   the atomizing device further comprises an accommodating tube, an atomizing tube, an accommodating cavity, an atomizing base, an air-intake pipe and an atomizer head, the atomizing tube is arranged in the accommodating tube, the atomizing base is disposed at the end of the accommodating tube away from the upper cover assembly, the accommodating cavity is formed among the accommodating tube, the atomizing tube and the atomizing base, the air-intake pipe is located in the accommodating cavity,
   the upper cover assembly comprises an upper cover, an upper cover connecting base and an air inlet defined on the upper cover, and the upper cover connecting base is fixedly connected between the upper cover and the atomizing device,
   the upper cover connecting base is provided with a fixing hole, the air-intake pipe extends through the fixing hole and is affixed in the fixing hole, and the other end of the air-intake pipe is disposed on the atomizing base,
   the collecting device comprises a retaining portion, a tubular body and a collecting slot, the retaining portion is bowl-shaped or funnel-shaped, and
   wherein the regulating ring is located at a bottom of the atomizing device, and configured to regulate an airflow flows to the bottom of the atomizing device through the air-intake pipe.

2. The atomizer according to claim 1, wherein an upper edge of the regulating ring bends inwardly to form a holding portion, the holding portion abuts an upper end of the regulating base, the holding portion is provided with the second circulating portion, the second circulating portion is at least partially aligned with the first circulating portion by rotating the regulating ring, which enables the atomizing device to be in fluid communication with the regulating assembly.

3. The atomizer according to claim 1, wherein one end of the tubular body extends towards the inside of the tubular body to form the retaining portion, and the retaining portion is fixedly connected to the tubular body to form the collecting slot.

4. The atomizer according to claim 3, wherein an angle formed between the tubular body and the retaining portion is between 0-90 degrees.

5. The atomizer according to claim 1, wherein one end of the atomizing tube is tightly fitted to the atomizer head, and the other end of the atomizing tube is disposed on the upper cover assembly.

6. The atomizer according to claim 5, wherein the atomizing base comprises a shoulder, a first connecting portion and a second connecting portion, the first connecting portion and the second connecting portion are connected to opposite ends of the shoulder respectively, the first connecting portion is connected to a connecting ring, the second connecting portion is connected to the regulating assembly, and the atomizer head is threadedly arranged onto the atomizing base by means of the connecting ring.

7. The atomizer according to claim 6, wherein the atomizing base is provided with a connecting tube, the connecting tube is sleeved on and in fluid communication with the air-intake pipe, the shoulder is provided with a through hole, the through hole is in fluid communication with the connecting tube, and the atomizer head is provided with an air vent in fluid communication with the through hole.

8. The atomizer according to claim 1, wherein the regulating base is provided with a stopping boss near an opening of the first circulating portion, the stopping boss protrudes into the second circulating portion to enable the regulating ring to rotate within a scope of a radian of the second circulating portion.

9. The atomizer according to claim 8, wherein the radian of the second circulating portion is larger than that of the first circulating portion.

10. An aerosol generating device, comprising the atomizer according to claim 1.

* * * * *